United States Patent [19]

Roman

[11] 4,024,138

[45] May 17, 1977

[54] ALPHA-(HALOPHENOXY)ACETYL NITROMETHYLENE TETRAHYDROTHIAZINES

[75] Inventor: Steven A. Roman, Oakdale, Calif.

[73] Assignee: Shell Oil Company, Houston, Tex.

[22] Filed: Apr. 26, 1976

[21] Appl. No.: 680,615

[52] U.S. Cl. .................. 260/243 R; 424/246; 71/90

[51] Int. Cl.² ..................... C07D 279/06

[58] Field of Search .............. 260/243 R; 424/246

[56] References Cited

UNITED STATES PATENTS 3,962,225  6/1976  Powell .................. 260/243

*Primary Examiner*—John M. Ford

[57] ABSTRACT

Novel compounds, identified in the title, useful as insecticides and herbicides.

1 Claim, No Drawings

ALPHA-(HALOPHENOXY)ACETYL NITROMETHYLENE TETRAHYDROTHIAZINES

DESCRIPTION OF THE INVENTION

It has been found that useful insecticidal and/or herbicidal properties are possessed by alpha-(halophenoxy)acetyl nitromethylene tetrahydrothiazines. These compounds are described by the formula:

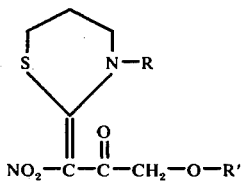

wherein R is hydrogen or middle halogen (i.e., chlorine and bromine) and R' is 2,4-dichlorophenyl, 2-methyl-4-chlorophenyl or 2,4,5-trichlorophenyl.

A preferred subclass of these compounds is that wherein R' is 2,4-dichlorophenyl.

For illustration, preparation of typical species esters of the genus is described in the examples included hereinafter. Other typical, illustrative species of this genus include those wherein the symbols represent the following moieties, this manner of naming these species being accurate, yet pointing out the differences between the different species more clearly than if the entire, complicated name of each species were to be given:
R = H, R' = 2-methyl-4-chlorophenyl 2,4,5-trichlorophenyl
R = Cl, R' = 2-methyl-4-chlorophenyl 2,4,5-trichlorophenyl R = Br, R' = 2-methyl-4-chlorophenyl 2,4,5-trichlorophenyl Compounds of this invention wherein R is hydrogen can be prepared by treating tetrahydro-2-(nitromethylene)-2H-1,3-thiazine with a 1-(R'-O-CH$_2$-carbonyl)-3-methylimidazolium chloride by the method described by E. Guibe-Jampel, et al., Bull. Soc. Chim. Fr. 1973 (3) (Pt. 2), pp. 1021–7. According to this method, the imidazolium chloride is prepared by treating 1-methylimidazole with the appropriate acid chloride, R'-O-CH$_2$-C(O)-Cl, preferably in a suitable solvent and at a low temperature, for example, about 0° C. A suitable general method for conducting this procedure comprises adding a solution of the acid chloride in tetrahydrofuran or monoglyme slowly (e.g., dropwise) to a cold (e.g., 0°) solution of the N-methylimidazole in the same solvent, stirring the cold mixture for a period of from about 15 minutes to one hour to ensure complete reaction, then adding to that stirred cold mixture a solution of the thiazine, then warming the stirred mixture to a temperature of from about room temperature to the reflux temperature, and stirring the warm mixture for a time to ensure complete reaction.

The desired product can be isolated from the crude reaction mixture and purified by conventional methods, such as filtration, extraction, crystallization and elution (chromatography).

The thiazine precursor can be prepared by treating 5,6-dihydro-2-(methylthio)-4H-1,3thiazine (A. F. McKay et al., J. Am. Chem. Soc., 80, 3339 (1958)) with an alkyl nitroacetate (S. Zen, et al., Kogyo Kagaku Zasshi, 74, 70 (1971)) in the presence of a catalytic amount of zinc ion (e.g., zinc chloride) to form the alkyl nitro(tetrahydro-2H-1,3-thiazine-2-ylidene)acetate, which is hydrolyzed with a base and decarboxylated by acidification to give the thiazine. The acid chlorides, R'-O-CH$_2$-C(O)-Cl, are a known class of compounds.

Compounds of the invention wherein R is halogen can be prepared by treating the unsubstituted precursor (R = H) with about a 10% molar excess of a halogen or a halogenated compound containing positive halogen at about room temperature, employing a halogenated alkane as solvent. Suitable halogenating agents include chlorine, bromine, N-chloro- and N-bromosuccinimide. Recovery of the product is conveniently effected by filtering the mixture, evaporating the solvent and recrystallizing the product. Other conventional techniques such as distillation, extraction, elution and the like can be used as appropriate.

Procedures for preparing compounds of this invention are illustrated in the following example of the preparation of a particular species thereof. In all cases, the identity of the product, and the identity of any intermediate involved were confirmed by appropriate chemical and spectral analyses.

EXAMPLE 1

3-(2,4-dichlorophenoxy)-1-nitro-1-(tetrahydro-2H-1,3-thiazin-2-ylidene)-2-propanone (1)

To a mixture of 235 g of 5,6-dihydro-2-methylthio)-4H-1,3-thiazine and 2 g of zinc chloride at approximately 115° in a nitrogen atmosphere, 263 g of ethyl nitroacetate was added dropwise over a 1.5 hour period. The mixture was held at 110°–120°. When evolution of methyl mercaptan ceased after 45 minutes further stirring of the heated mixture, 1 g of zinc chloride was added and the mixture was stirred at about 115° for 1.25 hours. An additional 1 g of zinc chloride then was added and stirring of the mixture at about 115° was continued for 1.5 hours. The mixture then was poured into a cooled solution of 2/1 ether/isopropyl alcohol mixture. The crystallized product was collected, washed with ether and dried under reduced pressure to leave a tan solid, m.p. 100°–102°, which on recrystallization from methanol gave ethyl nitro(tetrahydro-2H-1,3-thiazin-2-ylidene)acetate (1A) as a pale yellow solid, m.p. 105°–106°.

2.3 g of 1A was added to 10 ml of 20% aqueous sodium hydroxide and the mixture was stirred at room temperature for 12 hours. The resulting solution was treated dropwise with 3.5 g of acetic acid. The addition was accompanied by vigorous gas evolution. The resulting mixture was extracted with methylene chloride and the extract was dried (magnesium sulfate) and concentrated under reduced pressure to give tetrahydro-2-(nitromethylene)-2H-1,3-thiazine (1B) as a pale yellow solid, m.p. 76°–78°.

A solution of 7.2 g of 2,4-dichlorophenoxymethyl acid chloride in 20 ml of tetrahydrofuran was added dropwise to a solution of 2.5 g of 1-methylimidazole in 80 ml of tetrahydrofuran, at 0°–5°. The resulting slurry was stirred for 30 minutes at 5° and then 4.8 g of 1B was added all at once. The resulting mixture was stirred for 18 hours. A further 0.5 molar equivalent of the imidazole complex in 50 ml of tetrahydrofuran was prepared and added to the mixture, at 5°. The resulting mixture was stirred for 3 hours, the temperature of the mixture being permitted to rise to room temperature; then the mixture was stirred overnight. The tetrahydrofuran was stripped off and the residue was treated with 200 ml of methylene chloride and 200 ml of water. The phases were separated, the water phase was extracted with methylene chloride, the methylene chloride solutions were combined, washed with water, then saturated sodium chloride solution and dried (MgSO$_4$). The solvent was evaporated. The resulting oil was passed through Florisil to give recovered imidazole and a mush. The latter was triturated with pentane, filtration giving 1, as a pale yellow solid, m.p.: 164°–164.5°.

EXAMPLE 2

1-(3-chlorotetrahydro-2H-1,3-thiazin-2-ylidene)-3-(2,4-dichlorophenoxy)-1-nitro-2-propanone (2)

3.6 g of 1 and 2.1 g of N-chlorosuccinimide were combined in 150 ml of carbon tetrachloride and the mixture was refluxed for 1 hour. The resulting mixture was filtered through Celite and the solvent was evaporated to give a liquid, which was triturated in ether, decolorized with activated charcoal and filtered through Celite and stripped of solvent to give a yellow cloudy liquid. This was passed through Florisil, using methylene chloride as eluent; then stripped to give an oil, which was kept in a refrigerator over a week-end. Part of the oil crystallized. On scratching, more crystals formed. Separation of the crystals gave 2, as bright yellow crystals, m.p. 103°–105°.

EXAMPLE 3

1-(3-bromotetrahydro-2H-1,3-thiazin-2-ylidene)-3-(2,4-dichlorophenoxy)-1-nitro-2-propanone (3)

3 was prepared as a yellow solid, m.p.: 126° (with decomposition) by a procedure similar to that described in Example 2, using N-bromosuccinimide. It was necessary to heat the reaction mixture to reflux to effect the reaction.

The compounds of this invention exhibit useful herbicidal and insecticidal activity.

The pre-emergence herbicidal activity of compounds of this invention were evaluated by planting seeds of barnyard grass, garden cress, downy brome, wild mustard, yellow foxtail, velvet leaf, soybean, grain sorghum, cotton and wheat in soil treated with test compound at a set dosage. The planted soil was held under controlled conditions of temperature, moisture, and light for 12 to 14 days. The amount of germination was then noted and the effectiveness of the test compound was rated visually, on the basis of a 0 to 9 scale, 0 rating indicating no effect, 9 indicating death of the seedlings or no germination.

Compound 1 was found to be moderately toxic to the cress and mustard, slightly toxic to the barnyard grass, brome, velvet leaf, cotton and sorghum and non-toxic to the foxtail, soybean and wheat. Compound 3 was quite toxic to all of the test plants. Compound 2 was quite toxic to the barnyard grass, cress, velvet leaf, foxtail and mustard; it was not tested against the other plants.

The post-emergence activity of compounds of this invention was evaluated by spraying 7-day old crabgrass plants, 10-day old pigweed plants, 7-day old downy brome plants, 10-day old wild mustard plants, 10-day old green foxtail plants, 10-day old grain sorghum plants, 14-day old cotton plants and 7-day old wheat plants to runoff with a liquid formulation of the test compound at two set dosages. The sprayed plants were held under controlled conditions for 10 to 11 days and the effect of the test compound was then evaluated visually, the results being rated on the 0 to 9 scale described above.

The activity pattern of Compounds 1 and 3 was similar: none to slight toxicity with respect to the crabgrass, brome, foxtail, sorghum and wheat; moderate activity with respect to the others. Compound 2 exhibited a similar pattern of activity with respect to the first six test plants.

When applied as a herbicide, a compound of the invention ordinarily is formulated with a carrier and/or a surface active agent.

By "carrier" is meant here a solid or fluid material, which may be inorganic or organic and of synthetic or natural origin, with which the herbicide is mixed or formulated to facilitate its application to the plant, seed, soil or other object to be treated, or its storage, transport or handling.

The surface-active agent may be an emulsifying agent or a dispersing agent or a wetting agent; it may be nonionic or ionic.

Any of the carrier materials or surface-active agents usually applied in formulating pesticides may be used, and suitable examples of these are to be found, for example, in U.K. specification No. 1,232,930.

The compositions may be formulated as wettable powders, dusts, granules, solutions, emulsifiable concentrates, emulsions, suspension concentrates or aerosols. Wettable powders are usually compounded to contain 25, 50 or 75% w of toxicant and usually contain, in addition to solid carrier, 3–10% w of a dispersing agent and, where necessary, 0–10% w of stabilizer(s) and/or other additives such as penetrants or stickers. Dusts are usually formulated as a dust concentrate having a similar composition to that of a wettable powder but without a dispersant, and are diluted in the field with further solid carrier to give a composition usually containing 1/2–10% w of toxicant. Granules are usually prepared to have a size between 10 and 100 BS mesh (1.676–0.152 mm), and may be manufactured by agglomeration or impregnation techniques. Generally, granules will contain 1/2–25% w active ingredient and 0–10% w of additives such as stabilizers, slow release modifiers and binding agents. Emulsifiable concentrates usually contain, in addition to the solvent and, when necessary, co-solvent, 10–50% w/v active ingredient, 2–20% w/v emulsifiers and 0–20% w/v of appropriate additives such as stabilizers, penetrants and corrosion inhibitors. Suspension concentrates are compounded so as to obtain a stable non-sedimenting, flowable product and usually contain 10–75% w active ingredient, 0.5–15% w of dispersing agents, 0.1–10% w of suspending agents such as protective colloids and thixotropic agents, 0–10% w of appropriate additives such as defoamers, corrosion inhibitors, stabilizers, penetrants and stickers, and as carrier, water or an organic liquid in which the active ingredient is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate with water, also are contemplated. The emulsions may be of the water-in-oil or of the oil-in-water type, and may have a thick "mayonnaise"-like consistency.

The compositions may also contain other ingredients, for example, other compounds possessing pesticidal, especially insecticidal, acaricidal, herbicidal or fungicidal properties.

The amount of the herbicide of this invention necessary to kill or inhibit the growth of plants is defined as the herbicidal amount. When the compounds are used as preemergence herbicides, an application rate of about 0.5 to about 20 pounds per acre is used, with about 1 to about 10 pounds per acre being preferred. When the compounds are used as post-emergence herbicides, an application rate of about 0.01 to about 20 pounds per acre of one or more active compounds per acre is used, with an application rate of about 0.1 to about 3 pounds per acre being preferred. This quantity will obviously vary with the individual species of herbicide, the plant species, type of formulation, environmental conditions and the like. Those versed in the herbicide field, can readily determine the effective amount for a particular set of condition.

Activity of compounds of this invention with respect to insects was determined by using standardized tests to establish the $LC_{50}$ dosage (in milligrams of test compound per 100 milliliters of solvent or liquid carrier required in the solution or suspension of test compound used) that was required to kill 50% of the test insects. The test insects were the housefly, corn earworm, pea aphid and 2-spotted spider mite. Activity with respect to mosquito larvae was determined by placing the larvae in water containing the test compound.

In tests that were conducted, Compound 1 was active with respect to corn earworm larvae and was essentially inactive with respect to houseflies, aphids, mites and mosquito larvae. Compound 2 was active with respect to houseflies, slightly active with respect to aphids, highly active with respect to corn earworms, and essentially inactive with respect to mites and mosquito larvae. Compound 3 showed activity with respect to houseflies, slight activity with respect to aphids and mosquito larvae; it was active with respect to corn earworm larvae.

When applied as an insecticide, a compound of the invention ordinarily is formulated with an adjuvant — that is, a carrier optionally a surface-active agent.

The term "carrier" in this regard means a material which may be inorganic or organic and of synthetic or natural origin with which the insecticide is mixed or formulated to facilitate its application to the plant, seed, soil and other object to be treated, or its storage, transport or handling. The carrier may be a solid or a liquid.

Suitable solid carriers may be natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as for example, carbon and sulfur; natural and synthetic resins such as for example, coumarone resins, polyvinyl chloride and styrene polymers and copolymers, solid polychlorophenols; bitumen, waxes such as beeswax, paraffin wax and chlorinated mineral waxes; degradable organic solids such as ground corn cobs and walnut shells; and solid fertilizers, for example, superphosphates.

Suitable liquid carriers include solvents for the compounds of this invention and liquids in which the toxicant is insoluble or only slightly soluble.

Examples of such solvents and liquid carriers generally are water, alcohols, for example, isopropyl alcohol, ketones, such as acetone, methyl ethyl ketone, methyl isobutyl ketone and cyclohexanone; ethers; aromatic hydrocarbons, such as benzene, toluene and xylene; petroleum fractions, such as kerosene, light mineral oils, chlorinated hydrocarbons, such as carbon tetrachloride, perchlorethylene, trichloroethane, including liquefied normally vaporous gaseous compounds. Mixtures of different liquids are often suitable.

If used, the surface-active agent may be an emulsifying agent or a dispersing agent or a wetting agent. It may be nonionic or ionic. Surface-active agents usually applied in formulating pesticides may be used. Examples of such surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; fatty acid salts of low molecular weight, mono-, di- and trialkylamines; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products; alkali or alkaline earth metal salts, preferably sodium salts, of sulfuric or sulfonic acids esters containing at least 10 carbon atoms in the molecule, for example, sodium lauryl sulfate, sodium secondary alkyl sulfates, sodium salts of sulfonated caster oil, and sodium alkyaryl sulfonates such as sodium dodecylbenzene sulfonate; and polymers of ethylene oxide and copolymers of ethylene oxide and propylene oxide.

The compositions may be formulated as wettable powders, dusts, granules, solutions, emulsifiable concentrates, emulsions, suspension concentrates or aerosols. Encapsulated formulations and controlled release formulations also are contemplated, as are bait formulations. Wettable powders are usually compounded to contain 25, 50 or 75% w of toxicant and usually contain, in addition to solid carrier, 3–10% w of stabilizer(s) and/or other additives such as penetrants or stickers. Dusts are usually formulated as a dust concentrate having a similar compositions to that of a wettable powder but without a dispersant, and are diluted in the field with further solid carrier to give a composition usually containing ½–10% w of toxicant. Granules may be manufactured by agglomeration or impregnation techniques. Generally, granules will contain ½–25% w toxicant and 0–10% w of additives such as stabilizers, slow release modifiers and binding agents. Emulsifiable concentrates usually contain, in addition to the solvent, and when necessary, co-solvent, 10–50% w/v toxicant, 2–20% w/v emulsifiers and 0–20% w/v of appropriate additives such as stabilizers, penetrants and corrosion inhibitors. Suspension concentrates are compounded so as to obtain a stable, non-sedimenting, flowable product and usually contain 10–75% w toxicant, 0–5% w of dispersing agents, 0.1–10% w of suspending agents such as protective colloids and thixotropic agents, 0–10% w of appropriate additives such as defoamers, corrosion inhibitors, stabilizers, penetrants and stickers, and as carrier, water or an organic liquid in which the toxicant is substantially insoluble; certain organic additives or inorganic salts may be dissolved in the carrier to assist in preventing sedimentation or as antifreeze agents for water.

Aqueous dispersions and emulsions, for example, compositions obtained by diluting a wettable powder or an emulsifiable concentrate with water, also are contemplated.

The compositions may also contain other ingredients, for example, other compounds possessing pesticidal, herbicidal or fungicidal properties, or attractants, such as pheromones, attractive food ingredients, and the like, for use in baits and trap formulations.

These compositions are applied in sufficient amount to supply the effective dosage of insecticide at the locus to be protected. This dosage is dependent upon many factors, including the carrier employed, the method and conditions of application, whether the formulation is present at the locus in the form of an aerosol, or as a film, or as discrete particles, the thickness of film or size of particles, the insect species to be controlled and the like, proper consideration and resolution of these factors to provide the necessary dosage of active material at the locus being within the skill of those versed in the art. In general, however, the effective dosage of insecticides of this invention at the locus to be protected — i.e. the dosage to which the insect contacts — is of the order of 0.001% to 0.5% based on the total weight of the formulation, though under some circumstances the effective concentration will be as little as 0.0001% or as much as 2%, on the same basis.

I claim:

1. A compund of the formula:

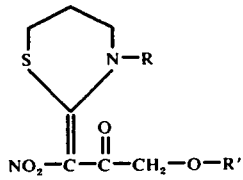

wherein R is hydrogen or middle halogen and R is 2,4-dichlorophenyl, 2-methyl-4-chlorophenyl or 2,4,5-trichlorophenyl.

* * * * *